US010556029B2

(12) United States Patent
Sabatake et al.

(10) Patent No.: US 10,556,029 B2
(45) Date of Patent: Feb. 11, 2020

(54) OZONE GENERATION DEVICE

(71) Applicant: Ushio Denki Kabushiki Kaisha, Tokyo (JP)

(72) Inventors: Kenichi Sabatake, Tokyo (JP); Naoki Goto, Tokyo (JP); Manabu Mori, Tokyo (JP); Takanori Jogi, Tokyo (JP)

(73) Assignee: USHIO DENKI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/324,488

(22) PCT Filed: Jul. 25, 2017

(86) PCT No.: PCT/JP2017/026819
§ 371 (c)(1),
(2) Date: Feb. 8, 2019

(87) PCT Pub. No.: WO2018/030144
PCT Pub. Date: Feb. 15, 2018

(65) Prior Publication Data
US 2019/0216962 A1 Jul. 18, 2019

(30) Foreign Application Priority Data

Aug. 9, 2016 (JP) .................. 2016-156690

(51) Int. Cl.
*A61L 2/20* (2006.01)
*A61L 9/015* (2006.01)
(Continued)

(52) U.S. Cl.
CPC .............. *A61L 2/202* (2013.01); *A61L 9/015* (2013.01); *C01B 13/10* (2013.01); *H01J 61/52* (2013.01);
(Continued)

(58) Field of Classification Search
CPC ...... A61L 2/202; A61L 9/015; A61L 2202/11; A61L 2209/212; A61L 9/205; A61L 9/20;
(Continued)

(56) References Cited

U.S. PATENT DOCUMENTS

2010/0143205 A1* 6/2010 Engelhard ............... A61L 9/205
422/121
2010/0209312 A1* 8/2010 Pastor .................... A61L 9/205
422/186.3

FOREIGN PATENT DOCUMENTS

JP H06-051244 U 7/1994
JP H07-187611 A 7/1995
(Continued)

OTHER PUBLICATIONS

International Search Report issued in PCT/JP2017/026819; dated Oct. 24, 2017.
(Continued)

*Primary Examiner* — Xiuyu Tai
(74) *Attorney, Agent, or Firm* — Studebaker & Brackett PC

(57) ABSTRACT

An ozone generation device has a casing; a wall body partitioning a space surrounded by the casing into at least a first chamber and a second chamber; a first opening and a second opening provided in a part of the casing to communicate an outer side of the casing and the first chamber; a blower communicating the first chamber and the second chamber; a third opening provided in a part of the casing to communicate the outer side of the casing and the second chamber; a light source body provided between the blower and the third opening in the second chamber and configured to emit ultraviolet light; and an electrical body provided in a position between the first opening and the second opening
(Continued)

in the first chamber and configured to supply electric power for driving the light source body.

20 Claims, 6 Drawing Sheets

(51) Int. Cl.
  *C01B 13/10* (2006.01)
  *H01J 61/52* (2006.01)
  *H01J 65/00* (2006.01)
(52) U.S. Cl.
  CPC .......... *H01J 65/00* (2013.01); *A61L 2202/11* (2013.01); *A61L 2209/212* (2013.01)
(58) Field of Classification Search
  CPC ........... C01B 13/10; H01J 61/52; H01J 65/00; Y10S 261/88
  See application file for complete search history.

(56) References Cited

FOREIGN PATENT DOCUMENTS

| | | |
|---|---|---|
| JP | 2001-342139 A | 12/2001 |
| JP | 2014-103028 A | 6/2014 |
| JP | 2014-226605 A | 12/2014 |
| JP | 2016-037416 A | 3/2016 |

OTHER PUBLICATIONS

Office Action issued in JP 2016-156690; mailed by the Japanese Patent Office dated Jan. 12, 2018.
Notification of Transmittal of Translation of the International Preliminary Report on Patentability and Translation of Written Opinion of the International Searching Authority; PCT/JP2017/026819; dated Feb. 21, 2019.

\* cited by examiner

OZONE GENERATION DEVICE

TECHNICAL FIELD

The present invention relates to an ozone generation device using an ultraviolet light source.

BACKGROUND ART

Gas containing ozone at a predetermined concentration has sterilizing and deodorizing effects and is used in various fields. A photochemical reaction using an ultraviolet light source is known as a method for generating such ozone.

An irradiation device using an excimer lamp as an ultraviolet light source is disclosed in, for example, Patent Document 1.

PRIOR ART DOCUMENT

Patent Document

Patent Document 1: JP-A-2014-103028

SUMMARY OF THE INVENTION

Problems to be Solved by the Invention

In a case of generating ozone using a photochemical reaction method, a low pressure mercury lamp has been used as an ultraviolet light source. However, the light emitted from the light source includes the wavelength for generating ozone and the wavelength for decomposing ozone. For this reason, the ozone generation and decomposition reactions occur at the same time, and oxygen atoms generated in the decomposition reaction react with the ozone, thus reducing the ozone, whereby extremely high concentration ozone cannot be generated.

Consideration is made to enhance the ozone generation efficiency by using an excimer lamp that emits light not including the ozone decomposition wavelength as a light source for ozone generation. The inventors of the present invention studied utilizing the light irradiation device disclosed in the above-mentioned Patent Document 1 as an ozone generation device.

FIG. 6 is a schematic perspective view of a light irradiation device disclosed in Patent Document 1. A light irradiation device 100 has a partition wall 103 provided inside a casing 101. The interior of the casing 101 is partitioned into an electrical body accommodating chamber 110 and a lamp accommodating chamber 120 by the partition wall 103. An end 103a of the partition wall 103 is in contact with a side wall 101a of the casing 101. A communication path 104 is formed between the end 103b of the partition wall 103 and a side wall 101b of the casing 101.

An electrical body 111 is accommodated in the electrical body accommodating chamber 110. An excimer lamp 121 including a long arc tube is accommodated in the lamp accommodating chamber 120. A light exit window 105 is formed in correspondence with the excimer lamp 121 in an upper wall 101c of the casing 101. The electrical body 111 supplies electric power necessary for causing the excimer lamp 121 to emit light to the excimer lamp 121.

A blower 113 is disposed at a position on the electrical body accommodating chamber 110 side of the side wall 101a of the casing 101. An exhaust port 123 is provided at a position on the lamp accommodating chamber 120 side of the side wall 101a of the casing 101. After the outside air of the casing 101 (the air) is suctioned into the electrical body accommodating chamber 110 by the blower 113 and cools the electrical body 111, the air flows toward the communication path 104 provided between the partition wall 103 and the side wall 101b of the casing 101. Thereafter, the air flows into the lamp accommodating chamber 120 via the communication path 104 and flows around the excimer lamp 121 to cool the excimer lamp 121, and then, is exhausted from the exhaust port 123.

The light emitted from the excimer lamp 121 is radiated to the outside through the light exit window 105. The ozone is inevitably generated from the oxygen contained in the air at the periphery of the excimer lamp 121. The ozone is exhausted from the exhaust port 123 together with the air that has cooled the excimer lamp 121. That is, since the ozone generated in the lamp accommodating chamber 120 is discharged to the outside from the exhaust port 123 without flowing to the electrical body accommodating chamber 110 side, the electrical body 111 is prevented from being contaminated and corroded by ozone.

As described above, Patent Document 1 merely relates to a light irradiation device, which should be understood from the fact that the light exit window 105 is provided. That is, in the device described in Patent Document 1, ozone is secondarily generated. The inventors of the present invention studied utilizing the light irradiation device 100 shown in FIG. 6 as an ozone generation device. However, in this configuration, the amount of ozone exhausted from the exhaust port 123 is insufficient for applications where the original ozone generation device is expected, such as sterilization and deodorization.

From the viewpoint of simply increasing the amount of ozone to be exhausted, a method of increasing the power of the blower 113 can be considered. However, in order to install the large-sized blower 113, the surface area of the casing 101 needs to be increased, and hence it becomes extremely larger than the light irradiation device 100 shown in FIG. 6.

In view of the above problem, it is an object of the present invention to provide an ozone generation device capable of exhausting a sufficient amount of ozone without including a large-sized blower.

Means for Solving the Problem

An ozone generation device of the present invention includes:
a casing;
a wall body that partitions a space surrounded by the casing into at least a first chamber and a second chamber;
a first opening and a second opening provided in a part of the casing to communicate an outer side of the casing and the first chamber;
a blower mounted at a position inside the wall body or outside the wall body to communicate the first chamber and the second chamber;
a third opening provided in a part of the casing to communicate the outer side of the casing and the second chamber;
a light source body provided between the blower and the third opening in the second chamber and configured to emit ultraviolet light; and
an electrical body provided at a position between the first opening and the second opening in the first chamber and configured to supply electric power for driving the light source body.

According to such a configuration, when the blower is driven, outside air is taken into the first chamber from the first opening and the second opening, and the outside air is sent to the second chamber by the blower. The outside air taken in through the first opening cools the electrical body. The outside air taken in from the first opening and cooling the electrical body, and the outside air taken in from the second opening are sent to the second chamber by the blower. Since the blower is provided at a position where the first chamber and the second chamber are communicated with each other, the air volume is large compared to that of the conventional configuration shown in FIG. 6 and the air is sent into the first chamber with speed. At least a part of the oxygen contained in the outside air is changed to ozone when irradiated with light emitted from the light source body. The ozone is discharged from the third opening. As described above, since the gas flowing in the second chamber has a large air volume and a high wind speed, the gas containing ozone is discharged to the outside of the device with sufficient air volume.

Therefore, according to the configuration of the present invention, even when a blower having the same size as the conventional configuration shown in FIG. 6 is provided, the gas containing a sufficient amount of ozone can be discharged to the outside of the device, and thus a small ozone generation device is realized.

According to such a configuration, a flow path from the blower side toward the third opening is formed in the second chamber, and the flow path in the opposite direction is excluded. The first chamber and the second chamber are separated by a wall body. Therefore, the ozone generated in the second chamber is suppressed from flowing into the first chamber accommodating the electrical body. In other words, contamination and corrosion of the electrical body by the ozone are suppressed.

Furthermore, according to such a configuration, the outside air taken in from the second opening is supplied into the second chamber without passing through the peripheral area of the electrical body, so that the function of cooling the light source body can be enhanced as compared with the conventional configuration.

In the above configuration, when the blower is driven, a first flow path for directing gas flowing into the first chamber from the outer side of the casing via the first opening toward the blower via the arrangement position of the electrical body, and a second flow path for directing gas flowing into the first chamber from the outer side of the casing via the second opening toward the blower without passing through the arrangement position of the electrical body may be formed.

Furthermore, in the above configuration, the first opening and the second opening may be provided on a same first surface of the casing, and the blower may be provided between the first surface of the casing and a second surface opposing the first surface of the casing and being located outside second chamber, and may be configured to blow air in a direction not parallel to the first surface from the first chamber toward the second chamber.

According to such a configuration, the outside air taken in from the second opening can be sent into the first chamber with a high wind speed. Therefore, the gas containing ozone generated in the second chamber can be discharged from the third opening while having a high wind speed.

In particular, the blower may be configured to be able to blow air in a direction perpendicular to the first surface from the first chamber to the second chamber.

In the above configuration, an electrical body accommodating unit that accommodates the electrical body in the first chamber, and a fourth opening that communicates the inner side of the electrical body accommodating unit and the blower may be further provided;

where the first opening may be provided so as to communicate the outer side of the casing and the inner side of the electrical body accommodating unit, and an area of the fourth opening may be smaller than an opening area of the blower.

According to this configuration, not only the outside air taken in from the first opening and having cooled the electrical body, but also the outside air taken in from the second opening and directed toward the blower without passing through the electrical body can be reliably sent to the first chamber. Since the second opening is arranged at a position closer to the blower than the first opening, the wind speed of the airflow toward the first chamber can be increased. Thus, the gas containing ozone generated in the first chamber can be discharged from the third opening while having a high wind speed.

The area of the open region on the primary side (first chamber side) of the blower and the area of the open region on the secondary side (second chamber side) of the blower may be the same or may be different. In the latter case, the area of the fourth opening may be smaller than the area of the open region on the primary side of the blower.

In the above configuration, the opening area of the blower may be smaller than a sum of an area of the second opening and an area of the fourth opening.

According to this configuration, since the opening area of the blower is smaller than the sum of the cross-sectional areas of the flow paths toward the primary side of the blower, the wind speed of the airflow from the blower toward the first chamber can be increased. Thus, the gas containing ozone generated in the first chamber can be discharged from the third opening while having a high wind speed.

The area of the open region on the primary side (first chamber side) of the blower and the area of the open region on the secondary side (second chamber side) of the blower may be the same or may be different. In the latter case, the area of the open region on the secondary side of the blower may be smaller than the sum of the area of the second opening and the area of the fourth opening.

In the above configuration, a power supply line for supplying electric power from the electrical body to the light source body may be further arranged, where the power supply line may be disposed closer to the blower than to the third opening as viewed from the light source body.

According to this configuration, a situation in which the power supply line is contaminated or corroded by the gas containing ozone generated in the first chamber can be suppressed.

Furthermore, the light source body may be covered by the casing, and may be configured so that light emitted from the light source body is not radiated to the outer side of the casing.

EFFECT OF THE INVENTION

According to the ozone generation device of the present invention, a large amount of ozone can be discharged with a small device.

MODE FOR CARRYING OUT THE INVENTION

Figure 1:
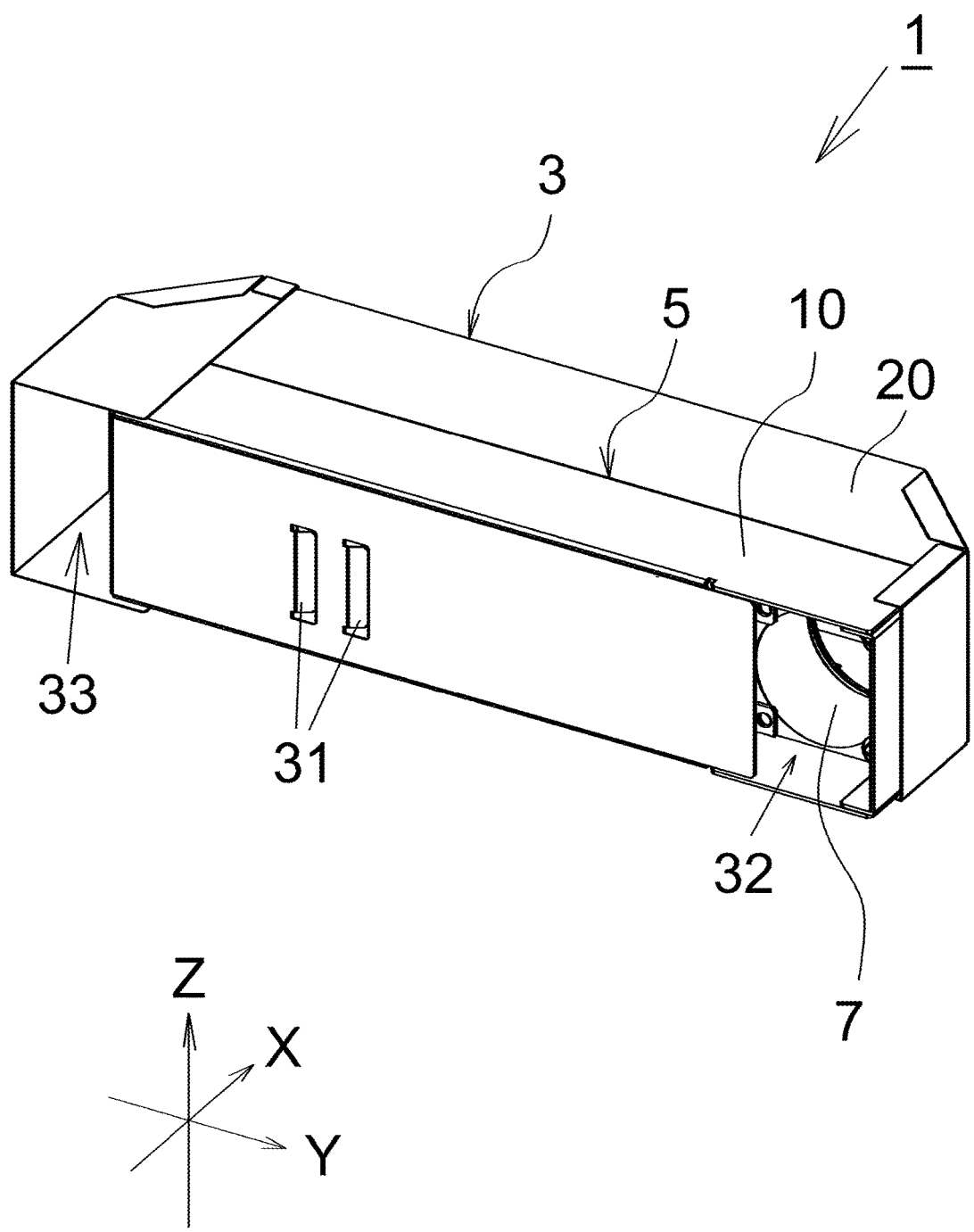
FIG. 1 is a schematic perspective view of one embodiment of an ozone generation device.

Hereinafter, an embodiment of an ozone generation device according to the present invention will be described with reference to the drawings. In each drawing below, the dimensional ratio in the drawing and the actual dimensional ratio do not necessarily coincide.

Figure 2:
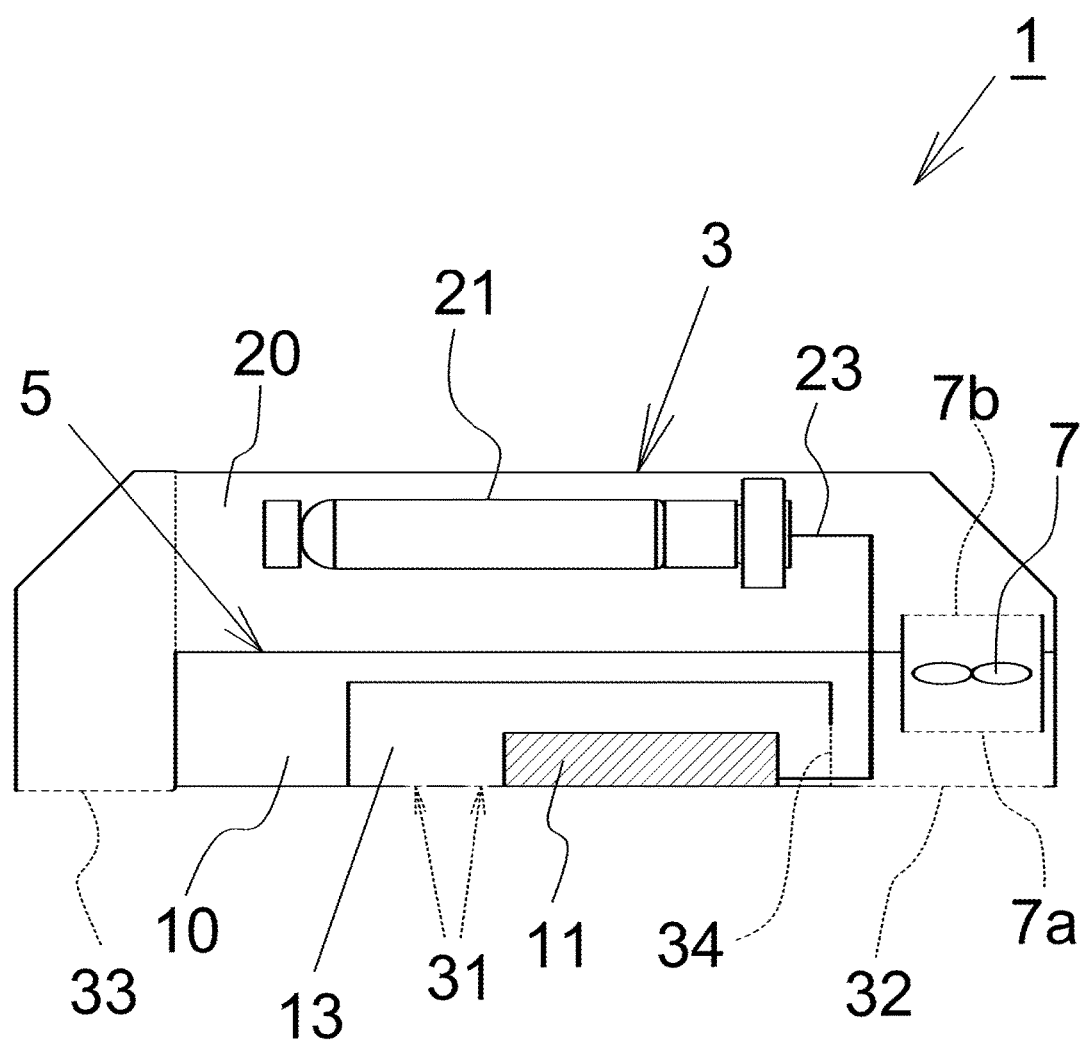
FIG. 2 is a schematic plan view of one embodiment of the ozone generation device.

FIG. 1 is a schematic perspective view of one embodiment of an ozone generation device according to the present invention. For convenience of explanation, a coordinate axis shown in FIG. 1 is taken. FIG. 2 is a schematic plan view of one embodiment of the ozone generation device of the present invention, and more specifically, corresponds to a figure in which an ozone generation device 1 shown in FIG. 1 is seen in a Z axis direction (more specifically, in the −Z axis direction). In FIG. 2, for the sake of convenience of explanation, the portion hidden on the inner side of the casing is also partially illustrated. Furthermore, in FIG. 2, an open region is shown by a broken line for the sake of convenience of explanation.

The ozone generation device 1 includes a casing 3 and a wall body 5 that separates a space surrounded by the casing 3. The space surrounded by the casing 3 is partitioned by the wall body 5 into a first chamber 10 and a second chamber 20 in an X axis direction. A blower 7 is disposed at a position communicating the first chamber 10 and the second chamber 20. In the ozone generation device 1 of the present embodiment, a part of the wall body 5 is hollowed, and the blower 7 is disposed in that place (see FIG. 2). The blower 7 may be disposed at a position between the wall body 5 and the side surface of the casing 3.

A first opening 31, a second opening 32, and a third opening 33 are provided at one portion of the casing 3. The first opening 31 and the second opening 32 communicate an outer side of the casing 3 and the first chamber 10. The third opening 33 communicates the outer side of the casing 3 and the second chamber 20.

The ozone generation device 1 includes a light source body 21 in the second chamber 20. More specifically, the light source body 21 is disposed at a position between the blower 7 and the third opening 33 in the second chamber 20. The light source body 21 is configured to radiate light in an ultraviolet region capable of generating ozone from air by photochemical reaction, and is configured by, for example, an excimer lamp. In addition to an excimer lamp, a low-pressure mercury lamp can also be used as the light source body 21. In the present embodiment, the ozone generation device 1 is covered with the casing 3, and the light emitted from the light source body 21 is configured so as not to be radiated to the outer side of the casing 3.

The ozone generation device 1 includes an electrical body 11 in the first chamber 10. More specifically, the electrical body 11 is disposed at a position between the first opening 31 and the second opening 32 in the first chamber 10. The electrical body 11 includes an electronic part that supplies the light source body 21 with electric power for driving the light source body 21. More specifically, the ozone generation device 1 includes a power supply line 23 that communicates the electrical body 11 and the light source body 21, so that the electric power is supplied from the electrical body 11 to the light source body 21 through the power supply line 23. In FIG. 2, for the sake of convenience of illustration, the power supply line 23 is indicated by a bold line. In the present embodiment, the power supply line 23 is disposed on the side opposite to the third opening 33 as seen from the light source body 21, that is, on the side close to the blower 7. That is, the power supply line 23 is disposed so as to be located between the light source body 21 and the blower 7.

In the present embodiment, the electrical body 11 is accommodated in an electrical body accommodating unit 13 disposed in the first chamber 10. The first opening 31 is formed so as to communicate the outer side of the casing 3 and the electrical body accommodating unit 13. The electrical body accommodating unit 13 has at least one part on the blower 7 side opened (fourth opening 34).

In the present embodiment, the first opening 31 and the second opening 32 are provided on the same surface of the casing 3. Furthermore, the blower 7 is disposed at a position between a surface of the casing 3 located on the side where the second opening 32 is formed and the surface of the casing 3 facing the relevant surface.

In the present embodiment, the area of the fourth opening 34 is smaller than the area of the open region (7a, 7b) of the blower 7. Furthermore, in the present embodiment, the area of the open region (7a, 7b) of the blower 7 is smaller than the sum of the area of the first opening 31 and the area of the second opening 32.

Figure 3:
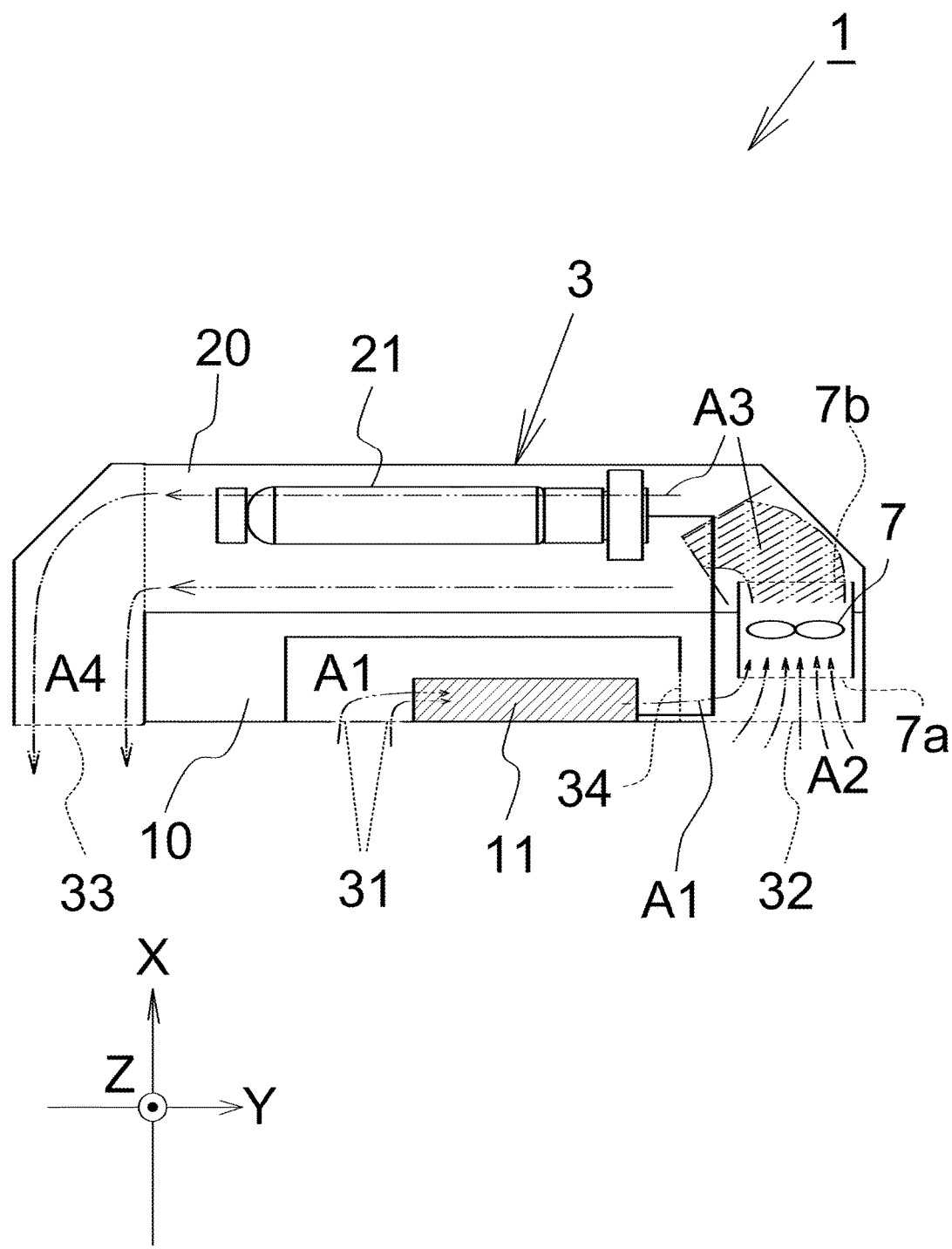
FIG. 3 illustrates airflow in the ozone generation device.

When the blower 7 is driven, air is taken into the ozone generation device 1 from the outer side of the casing 3 through the first opening 31 and the second opening 32. The airflow at this time will be described with reference to FIG. 3. FIG. 3 shows the airflow in the drawing of FIG. 2 with an arrowed chain double dashed line. For the sake of convenience of illustration, description on some of the reference numerals shown in FIG. 2 will be omitted in FIG. 3.

When the blower 7 is driven, the air A1 flows into the first chamber 10 from the outer side of the casing 3 through the first opening 31, and the air A2 flows into the first chamber 10 from the outer side of the casing 3 through the second opening 32. The air A1 that flowed in through the first opening 31 cools the electrical body 11 via the disposing position of the electrical body 11 and then reaches a primary side open region 7a of the blower 7 through the fourth opening 34. The air A2 that flowed in from the second opening 32 reaches the primary side open region 7a of the blower 7 without being directed to the disposing position of the electrical body 11. That is, in the primary side open region 7a of the blower 7, the air A1 taken in through the first opening 31 and the air A2 taken in from the second opening 32 are merged and taken in. Such air is sent into the second chamber 20 from a secondary side open region 7b of the blower 7.

The air sent out from the blower 7 flows through the second chamber 20 toward the third opening 33. As described above, the blower 7 is provided at a position of communicating the first chamber 10 and the second chamber 20. Therefore, the air A3 discharged from the secondary side open region 7b of the blower 7 can be sent out into the second chamber 20 with a momentum. Since this air A3 has a high wind speed, the air A3 flows through the second chamber 20 toward the third opening 33 while having a high wind speed. Then, in the second chamber 20, the air A3 is irradiated with the ultraviolet light emitted from the light source body 21, whereby a part of the air changes to ozone and gas A4 containing ozone is generated. The gas A4 still flows with a momentum toward the third opening 33, and is discharged to the outside of the ozone generation device 1 from the third opening 33.

That is, according to the ozone generation device 1, the gas A4 containing a sufficient amount of ozone can be discharged to the outside of the device from the third opening 33 by the small blower 7. Since the air A1 is taken in through the first opening 31, the function of cooling the electrical body 11 is also secured.

Furthermore, the ozone generation device 1 of the present embodiment is configured so that the area of the open regions (7a, 7b) of the blower 7 is smaller than the sum of the area of the first opening 31 and the area of the second opening 32. Thus, the air A3 can be sent out from the secondary side open region 7b of the blower 7 into the second chamber 20 with a still higher wind speed.

Furthermore, the ozone generation device 1 of the present embodiment is configured so that the area of the fourth opening 34 is smaller than the area of the open regions (7a, 7b) of the blower 7. With this configuration, air having sufficient air volume can be taken into the inside of the casing 3 from the second opening 32.

[Another Embodiment]

Hereinafter, another embodiment will be described.

Figure 4:
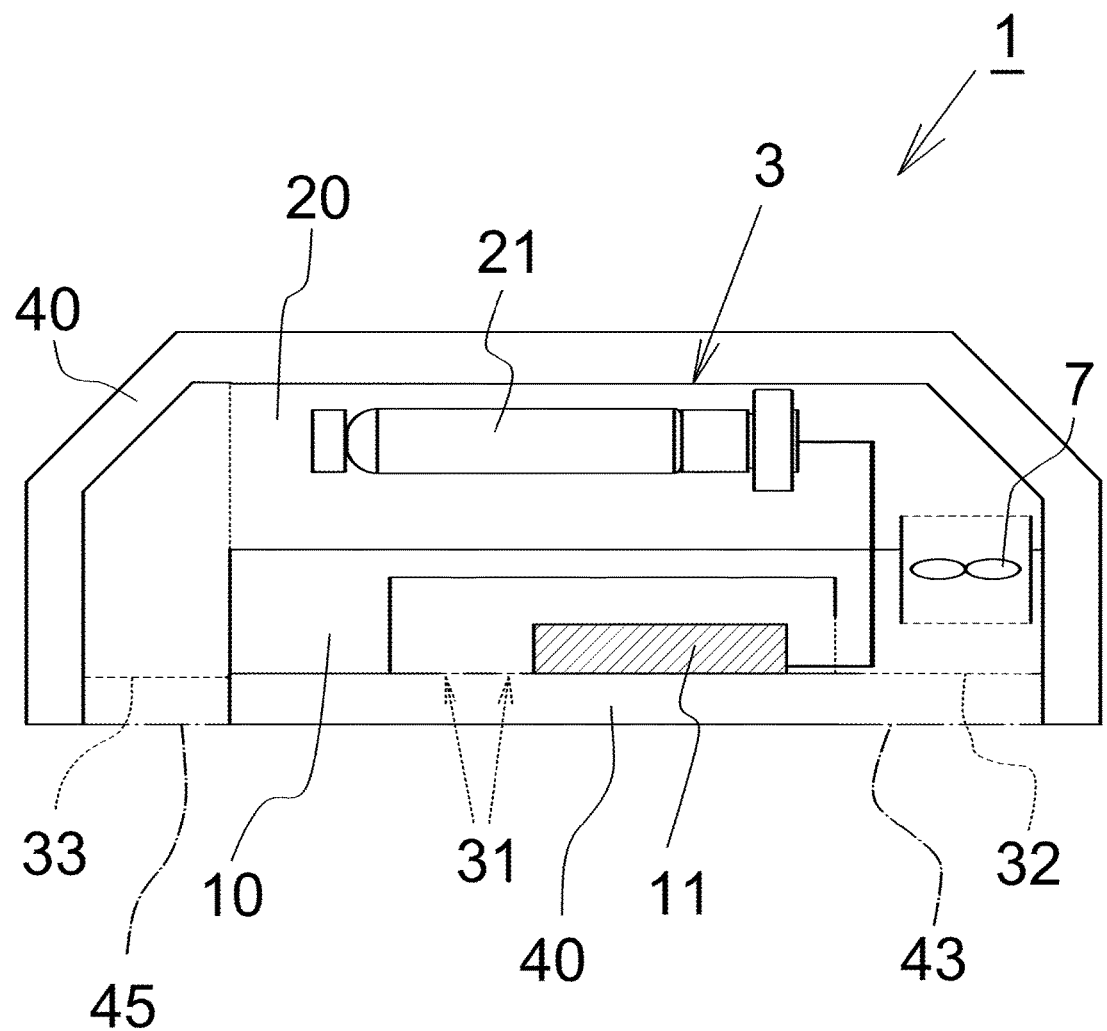
FIG. 4 is a schematic plan view of another embodiment of the ozone generation device of the present invention.
Figure 4:
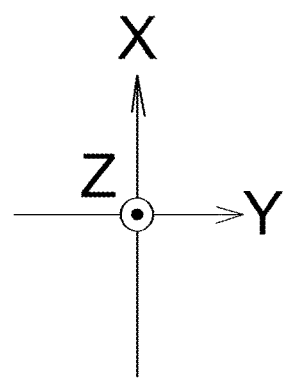

<1> As shown in FIG. 4, the ozone generation device 1 may include a cover unit 40 that covers the outer periphery of the casing 3. In this case, the cover unit 40 may also be provided with a predetermined opening. In the example shown in FIG. 4, an opening 43 and an opening 45 are provided in the cover unit 40. In FIG. 4, the openings (43, 45) are indicated by chain dashed lines. Air outside the cover unit 40 is taken in from the opening 43 and is headed toward the first opening 31 and the second opening 32. The gas containing ozone generated in the second chamber 20 is discharged to the outside of the ozone generation device 1 through the third opening 33 and the opening 45.

<2> In the above-described embodiment, the electrical body 11 is accommodated in the electrical body accommodating unit 13 in the first chamber 10, but it may be directly accommodated in the first chamber 10. In this case, in the first chamber 10, a ventilation path toward the blower 7 as viewed from the electrical body 11 may correspond to the fourth opening 34.

<3> In the above-described embodiment, the first opening 31 and the second opening 32 are provided on the same surface of the casing 3, but they may be provided on different surfaces, respectively. Furthermore, at least one of the first opening 31 and the second opening 32 may be provided on a plurality of surfaces of the casing 3. For example, in the ozone generation device 1 shown in FIG. 1, the first opening 31 is provided only on the surface of the casing 3 parallel to the YZ plane, but the first opening 31 may be provided on the surface of the casing 3 parallel to the XY plane.

Furthermore, in the above-described embodiment, the case where the third opening 33 is provided on the surface on the side same as the surface of the casing 3 in which the first opening 31 and the second opening 32 are formed has been described, but the arrangement position of the third opening 33 is not limited thereto. For example, in the configuration shown in FIG. 1, the opening face of the third opening 33 may be a structure parallel to the XZ plane.

<4> In the ozone generation device 1 of the above-described embodiment, both the airflow in the first chamber 10 and the airflow in the second chamber 20 are in a direction substantially parallel to the Y axis. This is because both the first chamber 10 and the second chamber 20 have substantially rectangular parallelepiped shapes and the longitudinal direction thereof is parallel to the Y axis. Such a configuration is preferable in terms of downsizing the ozone generation device 1.

However, in the present invention, the shapes of the first chamber 10 and the second chamber 20 are not limited to the above-described embodiments. For example, the first chamber 10 may have a shape extending in the Y direction, and the second chamber 20 may have a shape extending in the X direction. Furthermore, the casing 3 may have a columnar body shape other than a rectangular parallelepiped shape, and the casing 3 may have a truncated pyramidal shape, a truncated conical shape, or a spherical shape.

<5> In the above-described embodiment, the power supply line 23 is disposed on the side closer to the blower 7 than to the third opening 33 as viewed from the light source body 21, but the configuration is not limited thereto. According to the configuration of the above-described embodiment, since the power supply line 23 is located in a pre-stage in which the gas containing ozone is generated in the second chamber 20, an effect of suppressing contamination and corrosion by the gas containing ozone can be expected.

Figure 5:
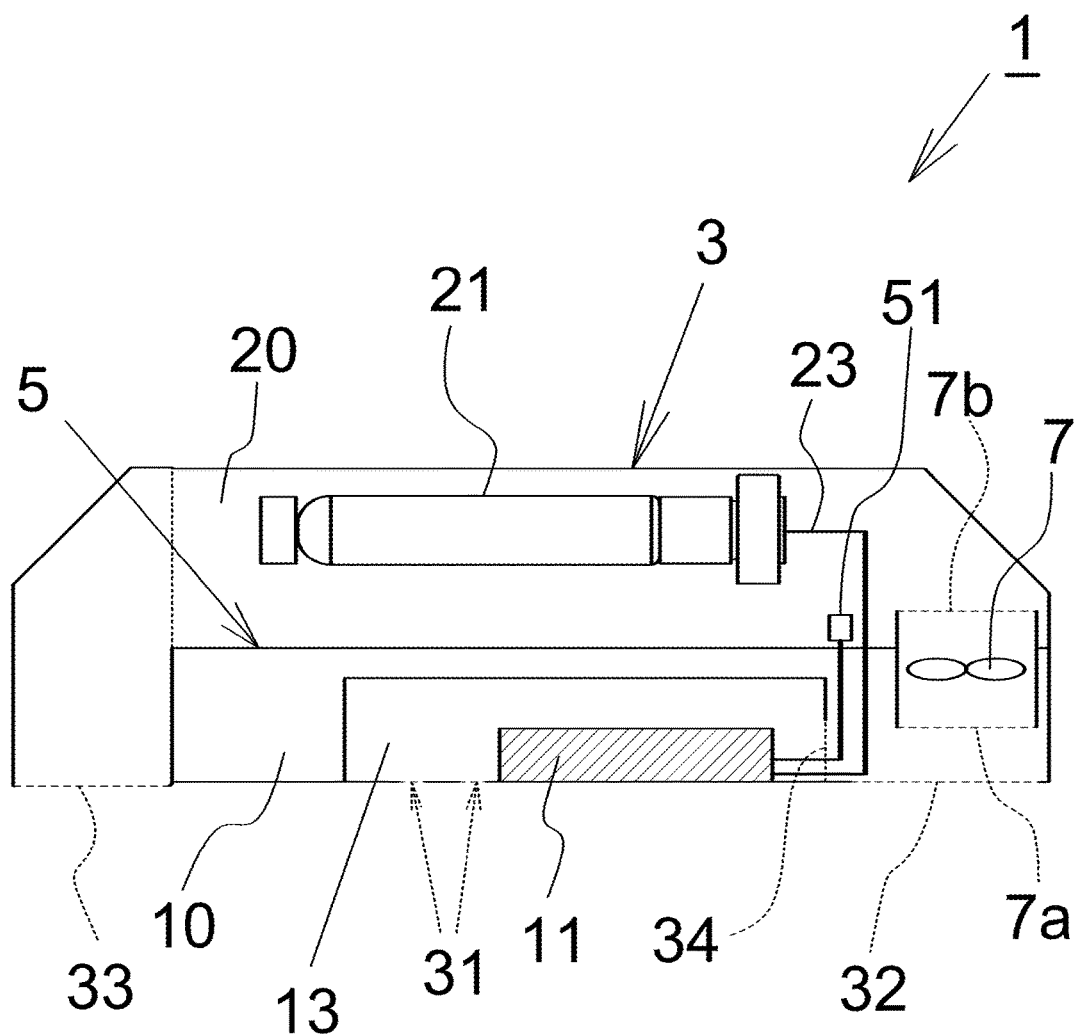
FIG. 5 is a schematic plan view of another embodiment of the ozone generation device.
Figure 5:
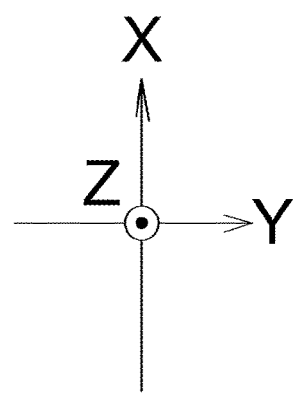
Figure 6:
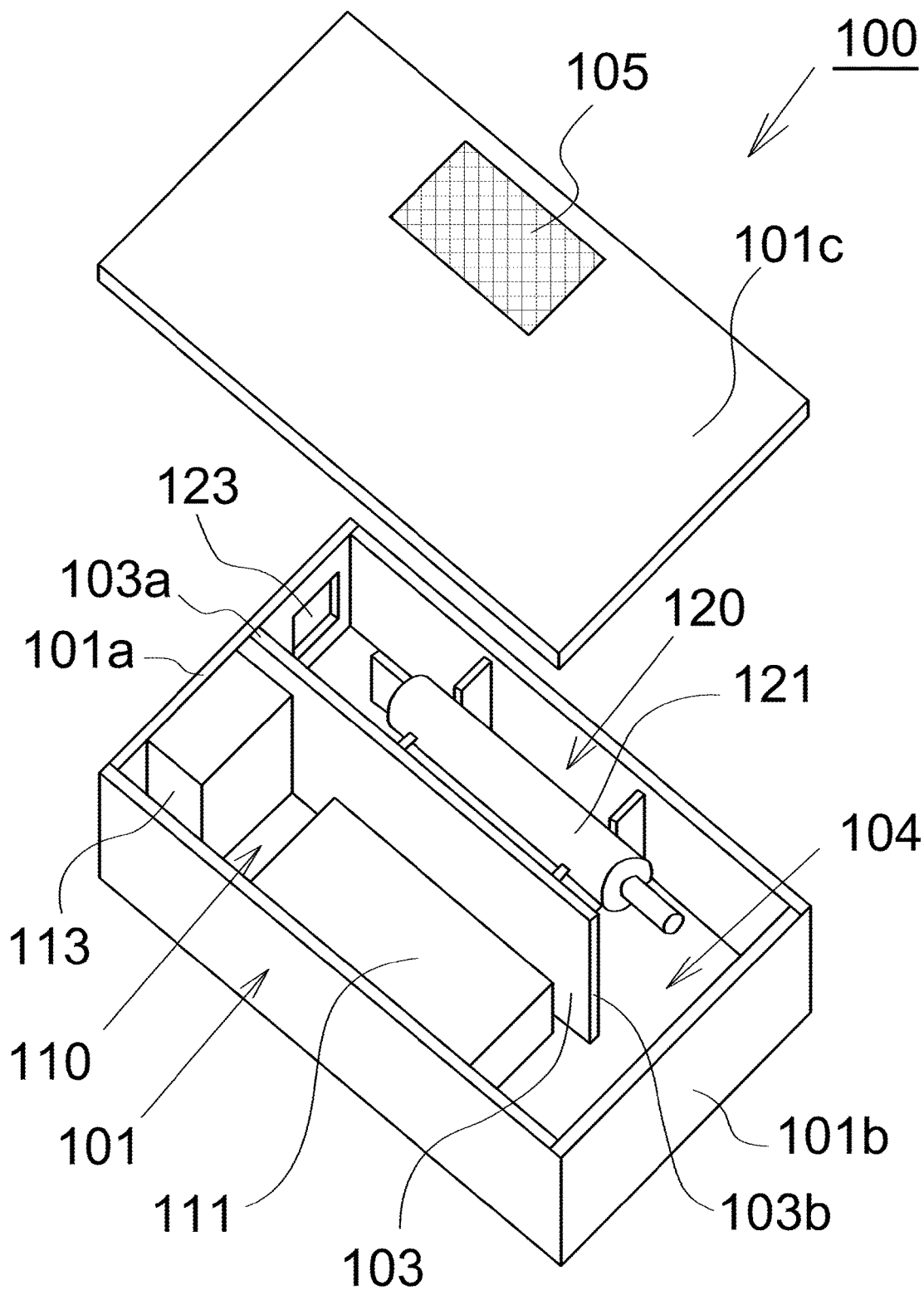
FIG. 6 is a schematic perspective view of a conventional light irradiation device.

<6> In the above-described embodiment, description has been made that the ozone generation device 1 is covered with the casing 3, and the light emitted from the light source body 21 is prevented from being radiated to the outer side of the casing 3. In this configuration, light from the outside of the ozone generation device 1 does not reach the light source body 21 disposed in the second chamber 20. At this time, a breakdown voltage of the light source body 21 increases due to the dark effect, and the light source body 21 may become difficult to drive. Therefore, as shown in FIG. 5, an auxiliary light source 51 for assisting the lighting of the light source body 21 may be provided in the second chamber 20. As the light emitted from the auxiliary light source 51 reaches the light source body 21, the adverse effect of the light source body 21 becoming difficult to drive can be avoided. A light emitting diode (LED), for example, can be used as the auxiliary light source 51. In the example shown in FIG. 5, an example in which the auxiliary light source 51 is supplied with electric power from the electrical body 11 is shown, but a power supply for the auxiliary light source 51 (not shown) may be provided at a place different from the electrical body 11.

<7> The area of the primary side open region 7a of the blower 7 and the area of the secondary side open region 7b do not necessarily need to be the same. At this time, the air A3 can be sent out from the blower 7 to the second chamber 20 with a high wind speed by setting the area of the secondary side open region 7b of the blower 7 smaller than the sum of the area of the first opening 31 and the area of the second opening 32. Furthermore, the air having sufficient air volume can be taken in from the second opening 32 to the inside of the casing 3 by making the area of the fourth opening 34 smaller than the area of the primary side open region 7a of the blower 7.

However, in the present invention, the relationship between the area of the open regions (7a, 7b) of the blower 7 and the area of each opening (31, 32, 34) is not limited to the above contents.

DESCRIPTION OF REFERENCE SIGNS 1 ozone generation device of the present invention
3 casing
5 wall body
7 blower
7a primary side open region of blower
7b secondary side open region of blower
10 first chamber
11 electrical body
20 second chamber
21 light source body
31 first opening
32 second opening
33 third opening
34 fourth opening
40 cover unit
43, 45 opening
51 auxiliary light source
100 conventional light irradiation device
101 casing
101a, 101b side wall of casing
101c upper wall of casing
103 partition wall
103a, 103b end of partition wall
104 communication path
105 light exit window
110 electrical body accommodating chamber
111 electrical body
120 lamp accommodating chamber
121 excimer lamp
123 exhaust port

The invention claimed is:

1. An ozone generation device comprising:
a casing;
a wall body partitioning a space surrounded by the casing into at least a first chamber and a second chamber;
a first opening and a second opening provided in a part of the casing to communicate an outer side of the casing and the first chamber;
a blower mounted at a position inside the wall body or outside the wall body to communicate the first chamber and the second chamber;
a third opening provided in a part of the casing to communicate the outer side of the casing and the second chamber;
a light source body provided between the blower and the third opening in the second chamber and configured to emit ultraviolet light; and
an electrical body provided in a position between the first opening and the second opening in the first chamber and configured to supply electric power for driving the light source body,
wherein the first opening and the second opening are provided at positions separated along a first direction and are communicated inside the first chamber,
the electrical body is provided at the position between the first opening and the second opening in the first chamber in the first direction, and
the third opening is provided on a side opposite to the second opening with respect to the first direction when the first opening is used as a reference.

2. The ozone generation device according to claim 1, wherein
when the blower is driven,
a first flow path for directing gas flowing into the first chamber from the outer side of the casing via the first opening toward the blower via an arrangement position of the electrical body, and
a second flow path for directing gas flowing into the first chamber from the outer side of the casing via the second opening toward the blower without passing through the arrangement position of the electrical body are formed.

3. The ozone generation device according to claim 1, wherein
the first opening and the second opening are provided on a same first surface of the casing, and
the blower is provided between the first surface of the casing and a second surface opposing the first surface of the casing and being located outside the second chamber, and is configured to blow air in a direction not parallel to the first surface from the first chamber toward the second chamber.

4. The ozone generation device according to claim 1, further comprising:
an electrical body accommodating unit that accommodates the electrical body in the first chamber, and
a fourth opening that communicates an inner side of the electrical body accommodating unit and the blower, wherein
the first opening is provided so as to communicate the outer side of the casing and the inner side of the electrical body accommodating unit, and
an area of the fourth opening is smaller than an opening area of the blower.

5. The ozone generation device according to claim 4, wherein the opening area of the blower is smaller than a sum of an area of the second opening and an area of the fourth opening.

6. The ozone generation device according to claim 1, further comprising a power supply line for supplying electric power from the electrical body to the light source body, wherein
the power supply line is disposed closer to the blower than to the third opening as viewed from the light source body.

7. The ozone generation device according to claim 1, wherein the light source body is covered by the casing, and is configured so that light emitted from the light source body is not radiated to the outer side of the casing.

8. The ozone generation device according to claim 2, wherein
the first opening and the second opening are provided on a same first surface of the casing, and
the blower is provided between the first surface of the casing and a second surface opposing the first surface of the casing and being located outside the second chamber, and is configured to blow air in a direction not parallel to the first surface from the first chamber toward the second chamber.

9. The ozone generation device according to claim 2, further comprising;
an electrical body accommodating unit that accommodates the electrical body in the first chamber, and
a fourth opening that communicates an inner side of the electrical body accommodating unit and the blower, wherein the first opening is provided so as to communicate the outer side of the casing and the inner side of the electrical body accommodating unit, and an area of the fourth opening is smaller than an opening area of the blower.

10. The ozone generation device according to claim 3, further comprising;

an electrical body accommodating unit that accommodates the electrical body in the first chamber, and a fourth opening that communicates an inner side of the electrical body accommodating unit and the blower, wherein the first opening is provided so as to communicate the outer side of the casing and the inner side of the electrical body accommodating unit, and an area of the fourth opening is smaller than an opening area of the blower.

11. The ozone generation device according to claim 9, wherein the opening area of the blower is smaller than a sum of an area of the second opening and an area of the fourth opening.

12. The ozone generation device according to claim 10, wherein the opening area of the blower is smaller than a sum of an area of the second opening and an area of the fourth opening.

13. The ozone generation device according to claim 2, further comprising a power supply line for supplying electric power from the electrical body to the light source body, wherein the power supply line is disposed closer to the blower than to the third opening as viewed from the light source body.

14. The ozone generation device according to claim 3, further comprising a power supply line for supplying electric power from the electrical body to the light source body, wherein the power supply line is disposed closer to the blower than to the third opening as viewed from the light source body.

15. The ozone generation device according to claim 4, further comprising a power supply line for supplying electric power from the electrical body to the light source body, wherein the power supply line is disposed closer to the blower than to the third opening as viewed from the light source body.

16. The ozone generation device according to claim 2, wherein the light source body is covered by the casing, and is configured so that light emitted from the light source body is not radiated to the outer side of the casing.

17. The ozone generation device according to claim 3, wherein the light source body is covered by the casing, and is configured so that light emitted from the light source body is not radiated to the outer side of the casing.

18. The ozone generation device according to claim 4, wherein the light source body is covered by the casing, and is configured so that light emitted from the light source body is not radiated to the outer side of the casing.

19. The ozone generation device according to claim 5, wherein the light source body is covered by the casing, and is configured so that light emitted from the light source body is not radiated to the outer side of the casing.

20. The ozone generation device according to claim 6, wherein the light source body is covered by the casing, and is configured so that light emitted from the light source body is not radiated to the outer side of the casing.

* * * * *